(12) United States Patent
Mul

(10) Patent No.: US 7,329,783 B2
(45) Date of Patent: Feb. 12, 2008

(54) HYDROFORMYLATION PROCESS

(75) Inventor: Wilhelmus Petrus Mul, Amsterdam (NL)

(73) Assignee: Shell Oil Company, Houston, TX (US)

( * ) Notice: Subject to any disclaimer, the term of this patent is extended or adjusted under 35 U.S.C. 154(b) by 27 days.

(21) Appl. No.: 11/427,247

(22) Filed: Jun. 28, 2006

(65) Prior Publication Data

US 2007/0015942 A1 Jan. 18, 2007

(30) Foreign Application Priority Data

Jun. 30, 2005 (EP) .................... 05254142

(51) Int. Cl.
*C07C 45/50* (2006.01)
*C07C 29/14* (2006.01)

(52) U.S. Cl. ............... 568/451; 568/454; 568/882

(58) Field of Classification Search ........... None
See application file for complete search history.

(56) References Cited

U.S. PATENT DOCUMENTS

| | | | |
|---|---|---|---|
| 3,369,050 A | 2/1968 | Greene | 260/632 |
| 3,420,898 A | 1/1969 | Van Winkle et al. | 260/632 |
| 3,440,291 A | 4/1969 | Van Winkle et al. | 260/632 |
| 3,448,157 A | 6/1969 | Slaugh et al. | 260/604 |
| 3,448,158 A | 6/1969 | Slaugh et al. | 260/604 |
| 3,501,515 A | 3/1970 | Van Winkle et al. | 260/439 |
| 3,904,547 A | 9/1975 | Aycock et al. | 252/414 |
| 5,112,519 A | 5/1992 | Giacobbe et al. | 252/174.21 |
| 5,728,893 A * | 3/1998 | Becker et al. | 568/454 |
| 6,482,990 B1 | 11/2002 | Sato et al. | 568/330 |
| 6,482,992 B2 | 11/2002 | Scholz et al. | 568/451 |

FOREIGN PATENT DOCUMENTS

| | | |
|---|---|---|
| EP | 0402051 | 5/1990 |
| WO | WO2005042458 | 5/2005 |
| WO | WO2005058786 | 6/2005 |

\* cited by examiner

*Primary Examiner*—Sikarl A. Witherspoon

(57) ABSTRACT

A hydroformylation process comprising reacting a feedstock composition comprising a compound having at least one olefinic carbon-to-carbon bond with hydrogen and carbon monoxide in the presence of an organophosphine modified cobalt hydroformylation catalyst, wherein the hydroformylation process is carried out in at least two reaction zones, wherein the at least two reaction zones comprise an earlier reaction zone and a later reaction zone, wherein the temperature of the later reaction zone is at least about 2° C. greater than the temperature in the earlier reaction zone, and the temperature of the later reaction zone is in the range of from about 140° C. to about 220° C., and the temperature of the earlier reaction zone is at least about 130° C.

15 Claims, No Drawings

HYDROFORMYLATION PROCESS

FIELD OF THE INVENTION

The present invention relates to a process for hydroformylating a compound having at least one olefinic carbon-to-carbon bond with carbon monoxide and hydrogen.

BACKGROUND OF THE INVENTION

Various processes for producing aldehyde and/or alcohol compounds by the reaction of a compound having at least one olefinic carbon-to-carbon bond with carbon monoxide and hydrogen in the presence of a catalyst are known. Typically, these reactions are performed at elevated temperatures and pressures. The aldehyde and alcohol compounds that are produced generally correspond to compounds obtained by the addition of a carbonyl or carbinol group, respectively, to an olefinically unsaturated carbon atom in the starting material with simultaneous saturation of the olefin bond. Isomerization of the olefin bond may take place to varying degrees under certain conditions. Thus, as a consequence of this isomerization, a variety of products may be obtained. These processes are typically known as hydroformylation reactions and involve reactions which may be shown in the general case by the following equation:

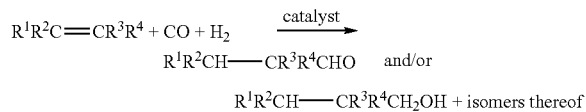

$$R^1R^2C=CR^3R^4 + CO + H_2 \xrightarrow{catalyst}$$
$$R^1R^2CH\text{---}CR^3R^4CHO \quad \text{and/or}$$
$$R^1R^2CH\text{---}CR^3R^4CH_2OH + \text{isomers thereof}$$

In the above equation, each group $R^1$ to $R^4$ may independently represent an organic radical, for example a hydrocarbyl group, or a suitable atom such as a hydrogen or halogen atom, or a hydroxyl group. The above reaction may also be applied to a cycloaliphatic ring having an olefinic linkage, for example cyclohexene.

The catalyst employed in a hydroformylation reaction typically comprises a transition metal, such as cobalt, rhodium or ruthenium, in complex combination with carbon monoxide and ligand(s) such as an organophosphine. Representative of the earlier hydroformylation methods which use transition metal catalysts having organophosphine ligands are described in U.S. Pat. No. 3,420,898, U.S. Pat. No. 3,501,515, U.S. Pat. No. 3,448,157, U.S. Pat. No. 3,440,291, U.S. Pat. No. 3,369,050 and U.S. Pat. No. 3,448,158.

In attempts to improve the efficiency of a hydroformylation process, attention has typically focussed on developing novel catalysts and novel processes for recovering and re-using the catalyst. In particular, novel catalysts have been developed which may exhibit improved stability at the required high reaction temperatures. Catalysts have also been developed which may permit the single-stage production of alcohols rather than a two-step procedure involving separate hydrogenation of the intermediate aldehyde. Moreover, homogeneous catalysts have been developed which may permit improved reaction rates whilst providing acceptable yields of the desired products.

Although organophosphine modified cobalt catalysts are known to be excellent catalysts in a single step hydroformylation reaction of olefinic compounds to alcohols, the use of such catalysts can also lead to the production of paraffins as a by-product. These paraffin by-products have very little commercial value. It would therefore be desirable to reduce the amount of paraffin by-products formed in the hydroformylation process using organophosphine modified cobalt catalysts.

Furthermore, we have detected that cobalt catalysts comprising cobalt in complex combination with carbon monoxide and an organophosphine ligand may decompose during the reaction to produce solid cobalt deposits such as cobalt and cobalt carbide (a compound of cobalt and carbon, empirical formula $Co_yC$, where y is in the range of from 2 to 3). Cobalt carbide is catalytically inactive in hydroformylation reactions. The presence of cobalt carbide also promotes further degradation of the cobalt catalyst, thereby resulting in an increased rate of catalyst usage. The cobalt carbide is not only catalytically inactive in hydroformylation reactions but also has a relatively bulky, porous structure and is insoluble in the reaction medium. This represents a significant disadvantage, particularly for homogeneous cobalt catalysts, because the cobalt carbide typically tends to agglomerate and form detrimental deposits on the internal surfaces of the production facility. The deposition of cobalt carbide impedes the running of a hydroformylation production facility with optimal efficiency. In particular, the deposition of cobalt carbide can cause plugging of the pipe work in the production facility, resulting in shut down of the production facility to allow for removal of these cobalt carbide deposits.

The present invention therefore seeks to provide a simple hydroformylation process which may be used in the single step conversion of olefinic compounds to alcohols, which not only reduces the amount of paraffin by-products produced, but also reduces the amount of cobalt catalyst lost through decomposition and formation of cobalt carbide and/or cobalt deposits on the internal surfaces of the production facility.

Additionally, since the demand for normal 1-alcohol products is greater than the demand for other alcohol products, it would also therefore be desirable to increase the proportion of normal 1-alcohols in the alcohol product composition.

U.S. Pat. No. 6,482,992 describes a process for the hydroformylation of olefins to give alcohols and/or aldehydes in a plurality of hydroformylation stages, each of which comprises: a) hydroformylating olefins having a carbon atom content of 6 to 24 carbon atoms in the presence of a cobalt- or rhodium catalyst in a reactor to the point of conversion of olefin reactant to product of 20 to 98%; b) removing the catalyst from the resulting liquid discharged from the reactor; c) separating the resulting liquid hydroformylation mixture into a low-boiler fraction comprising olefins and paraffins, and a bottoms fraction comprising aldehydes and/or alcohols; and d) reacting the olefins present in the low-boiler fraction in subsequent process stages comprising steps a, b and c and combining the bottoms fractions of process steps c) of all process stages. Different reaction conditions can be set in the hydroformylation reactors.

U.S. Pat. No. 5,112,519 describes a process for hydroformylation of olefins having the formula $(C_3)_x$, $(C_4)_x$ or mixtures thereof, where x has the value of 1 to 10, using a catalyst with a phosphine ligand at a temperature sufficient to promote reaction while retarding paraffin formation. A hydroformylation process disclosed in U.S. Pat. No. 5,112,519 is conducted in a single reactor, wherein the hydroformylation temperature is held at 135° C. for 2 hours, followed by a reaction temperature of 160° C. for 48 hours (Example 2). The reason for the use of the initially lower temperature is stated as isomerising the double bond of the olefins to the chain end.

SUMMARY OF THE INVENTION

According to the present invention, there is provided a hydroformylation process comprising reacting a feedstock composition comprising a compound having at least one olefinic carbon-to-carbon bond with hydrogen and carbon monoxide in the presence of an organophosphine modified cobalt hydroformylation catalyst, wherein the hydroformylation process is carried out in at least two reaction zones, wherein the at least two reaction zones comprise an earlier reaction zone and a later reaction zone, wherein the temperature of the later reaction zone is at least about 2° C. greater than the temperature in the earlier reaction zone, and the temperature of the later reaction zone is in the range of from about 140° C. to about 220° C., and the temperature of the earlier reaction zone is at least about 130° C.

DETAILED DESCRIPTION OF THE INVENTION

The hydroformylation process of the present invention is carried out in at least two reaction zones.

By the term "reaction zone" as used herein, is meant a controlled environment which contains the reaction mixture, wherein the hydroformylation process of the present invention may occur. A reaction zone can be, for example, a reactor or a section of a reactor in which the reaction conditions may be controlled independently from the rest of the reactor. Typically, the reaction zones are reactors.

The number of reaction zones used in order to carry out the process of the present invention is not critical, provided that at least two reaction zones are used. Typically, the number of reaction zones used in the present invention is at most 60, preferably at most 40, more preferably at most 20, and most preferably at most 10.

When the reaction zones of the process of the present invention are reactors, the reactors may be isolated reactors or a series of reactors which are linked together. Preferably the process of the present invention is carried out in at least two reactors linked in series. By the term "linked in series" as used herein, it is meant a series of separate reaction zones which are linked together so as to form a continuous reaction chain where the reaction mixture passes continuously from one reaction zone to the next under controlled temperature and pressure conditions, wherein the temperature and pressure of the individual reaction zones may be set independently.

The at least two reaction zones used herein comprise an earlier reaction zone and a later reaction zone. The earlier reaction zone can be the first reaction zone of the process of the present invention, but could also be a later reaction zone (e.g. the second or third reaction zone). The later reaction zone can be the second reaction zone of the process of the present invention, but could alternatively be a later reaction zone (e.g. the third or fourth reaction zone). Importantly, the earlier reaction zone comes before the later reaction zone, however, the earlier reaction zone need not be immediately adjacent to the later reaction zone. For example, the earlier reaction zone may be the first reaction zone and the later reaction zone may be the second reaction zone. Alternatively, the earlier reaction zone may be the first or second reaction zone and the later reaction zone may be the fourth or fifth reaction zone. In a preferred embodiment herein, the earlier reaction zone is the first reaction zone and the later reaction zone is the second, third, fourth, fifth, sixth, seventh or eighth reaction zone.

In a particularly preferred embodiment herein, none of the reaction zones preceding the later reaction zone is at a temperature higher than about 2° C. lower than the temperature of the later reaction zone.

Temperature staging is applied to the reaction zones in the process of the present invention, such that a temperature increase from a lower temperature in an earlier reaction zone to a higher temperature in a later reaction zone occurs. In particular, the temperatures of the reaction zones of the process of the present invention are controlled such that the temperature of the later reaction zone is at a temperature which is at least about 2° C. greater than the temperature in the earlier reaction zone, and wherein the temperature of the later reaction zone is in the range of from about 140° C. to about 220° C., and the temperature of the earlier reaction zone is at least about 130° C.

Preferably, the temperature of the later reaction zone will be in the range of from about 145° C. to about 215° C., more preferably from about 150° C. to about 210° C., and most preferably from about 155° C. to about 205° C.

The temperature of the earlier reaction zone will be at least about 130° C., preferably at least about 135° C., more preferably at least about 140° C. The temperature of the earlier reaction zone will preferably be no more than about 210° C., more preferably no more than about 200° C., and even more preferably no more than about 190° C. It is also required that the temperature of the earlier reaction zone will be at a temperature of at least about 2° C., preferably at least about 4° C., more preferably at least about 6° C., most preferably at least about 8° C., especially at least about 10° C., lower than the temperature of the later reaction zone. Typically, the temperature of the earlier reaction zone is at most about 90° C., more typically at most about 80° C., commonly at most about 70° C., lower than the temperature of the later reaction zone.

An example of the present invention in its simplest form would comprise only two reaction zones, wherein the first reaction zone is at a temperature of at least about 130° C., for example at a temperature in the range of from about 165° C. to about 185° C., and the second reaction zone is at a temperature in the range of from about 140° C. to about 220° C., for example at a temperature in the range of from about 185° C. to about 205° C., wherein the temperature of the second reaction zone is at least about 2° C. higher than the temperature of the first reaction zone. For example the temperature of the first reaction zone is 175° C. and the temperature of the second reaction zone is 195° C.

However, typically the present invention will comprise more than two reaction zones. For example, in an embodiment wherein the process of the present invention comprises four reaction zones, the first two reaction zones may be at a temperature of at least about 130° C., for example at a temperature in the range of from about 165° C. to about 185° C., e.g. 180° C., and the third and fourth reaction zones may be at a temperature in the range of from about 140° C. to about 220° C. and which is also at least about 2° C. higher than the first two reaction zones, for example at a temperature in the range of from about 185° C. to about 205° C., e.g. 190° C.

Overall, the process of the present invention will comprise an increase in temperature up to a maximum temperature in the range of from about 140° C. to about 220° C. After the maximum temperature in the range of from about 140° C. to about 220° C. has been attained, the temperature of any subsequent reaction zones may remain constant or be decreased.

In one embodiment of the present invention, the temperature may increase in a step-wise fashion from one reaction zone to the next; the increase in temperature may occur in a linear, asymptotic, exponential or any other manner. For example, in an embodiment wherein the process of the present invention comprises five reaction zones, the first reaction zone may be at a temperature of at least about 130° C. (for example, in the range of from about 150° C. to about 160° C., e.g. 155° C.), the second reaction zone may be at a temperature which is higher than the first reaction zone (for example, in the range of from about 160° C. to about 170° C., e.g. 165° C.), the third reaction zone may be at a temperature which is higher than the second reaction zone (for example, in the range of from about 170° C. to about 180° C., e.g. 175° C.), the fourth reaction zone may be at a temperature which is higher than the third reaction zone (for example, in the range of from about 180° C. to about 190° C., e.g. 185° C.), and the fifth reaction zone may be at a temperature which is higher than the fourth reaction zone (for example, in the range of from about 190° C. to about 200° C., e.g. 195° C.).

In another embodiment of the present invention, the temperature of the reaction zones subsequent to the reaction zone wherein the maximum temperature has been reached is reduced relative to the maximum temperature reached. For example, in an embodiment wherein the process of the present invention comprises six reaction zones, the first two reaction zones may be at a temperature of at least about 130° C., for example at a temperature in the range of from about 140° C. to about 160° C. (e.g. 155° C.), the third and fourth reaction zones may be at a temperature in the range of from about 140° C. to about 220° C. and which is also at least about 2° C. higher than the first two reaction zones, for example at a temperature in the range of from about 185° C. to about 205° C. (e.g. 200° C.), and the fifth and sixth reaction zones may be at a temperature which is lower than the third and fourth reaction zones, for example at a temperature in the range of from about 140° C. to about 180° C. (e.g. 170° C.). Alternatively, in an embodiment wherein the process of the present invention comprises seven reaction zones, the first and second reaction zones may be at a temperature of at least about 130° C., for example at a temperature in the range of from about 165° C. to about 185° C. (e.g. 180° C.), the third, fourth and fifth reaction zones may be at a temperature in the range of from about 140° C. to about 220° C. and which is also at least about 2° C. higher than the first reaction zone, for example at a temperature in the range of from about 185° C. to about 205° C. (e.g. 200° C.), the sixth reaction zone may be at a temperature which is lower than the third, fourth and fifth reaction zones, for example at a temperature in the range of from about 165° C. to about 185° C. (e.g. 180° C.), and the seventh reaction zone may be at a temperature which is higher than the sixth reaction zone but is lower than the third, fourth and fifth reaction zones, for example at a temperature in the range of from about 185° C. to about 205° C. (e.g. 190° C.).

In another embodiment of the process of the present invention wherein the process comprises eight reaction zones, the first two reaction zones may be at a temperature of at least about 130° C., for example at a temperature in the range of from about 160° C. to about 180° C. (e.g. 170° C.), the third reaction zone may be at a temperature lower than the first two reaction zones, for example at a temperature in the range of from about 140° C. to about 160° C. (e.g. 155° C.), the fourth, fifth and sixth reaction zones may be at a temperature in the range of from about 140° C. to about 220° C. and which is also at least about 2° C. higher than the first two reaction zones, for example at a temperature in the range of from about 180° C. to about 200° C. (e.g. 195° C.), and the seventh and eighth reaction zones may be at a temperature which is lower than the fourth, fifth and sixth reaction zones for example at a temperature in the range of from about 160° C. to about 180° C. (e.g. 175° C.).

In an alternative embodiment, when the earlier reaction zone is preceded by at least one reaction zone, the temperature in said preceding reaction zone may optionally be lower than the minimum temperature defined for the earlier reaction zone. For example, the earlier reaction zone may be preceded by a reaction zone which is at room temperature (i.e. 25° C.). Furthermore, the use of a temperature lower than the minimum temperature defined for the earlier reaction zone in any reaction zone in the reactor series is not excluded by the present invention. However, it is preferred that the process of the present invention is performed in at least two reaction zones, wherein no reaction zone is at a temperature lower than the minimum temperature defined for the earlier reaction zone.

The use of a temperature in the earlier reaction zone, which is at least about 2° C. lower than the temperature of the later reaction zone in a hydroformylation process using an organophosphine modified cobalt catalyst results in a lower paraffin by-product formation in the overall hydroformylation process when compared with a hydroformylation process wherein there is no such reduction in the temperature of the earlier reaction zone.

Also, it has been surprisingly observed that the use of a temperature in the earlier reaction zone, which is at least about 2° C. lower than the temperature of the later reaction zone in a hydroformylation process using an organophosphine modified cobalt catalyst results in an increased proportion of normal 1-alcohols compared to other alcohols produced in the overall hydroformylation process when compared with a hydroformylation process wherein there is no such reduction in the temperature of the earlier reaction zone. By the term "normal 1-alcohol" as used herein, it is meant the alcohol product is formed by a hydroformylation occurring upon a terminal carbon atom of the olefinic feedstock compound. In the case where the olefinic feedstock compound is a linear olefinic feedstock compound, the normal 1-alcohol would be linear 1-alcohol.

Since the rate of hydroformylation increases with increasing temperature, the use of the reduced temperature in the earlier reaction zone results in a decrease in overall reaction rate when compared with a hydroformylation process wherein there is no reduction in the temperature of the earlier reaction zone. The overall reaction rate also increases with increasing catalyst concentration. Therefore, any decrease in reaction rate due to the use of the reduced temperature in the earlier reaction zone can be compensated for by using an increased catalyst concentration.

The use of the lower temperature in the earlier reaction zone results in a reduction in the rate at which the catalyst degrades in the overall hydroformylation process when compared with a hydroformylation process wherein there is no reduction in the temperature of the earlier reaction zone.

In particular, the loss of cobalt through deposition of cobalt and/or cobalt carbide on the internal walls of the reactors is significantly reduced when compared with a hydroformylation process wherein there is no reduction in the temperature of the earlier reaction zone. This reduction in deposition of cobalt and/or cobalt carbide on the internal walls of the reactors results in a significant improvement in the overall process reliability due to the reduction in plugging and fouling of the reactors and pipe work which these cobalt deposits can cause. Therefore, operating the earlier reaction zone at a reduced temperature in the process of the present invention can result in a reduction in the amount of time that the reactors are shut down to allow for the removal of these cobalt deposits.

The process of the present invention may be carried out at various pressures. Consequently, hydroformylation in accordance with the process of the present invention may typically be carried out at pressures below about $7 \times 10^6$ Pa, to as low as about $1 \times 10^5$ Pa. The process of the present invention is, however, not limited in its applicability to the lower pressures. Pressures in the broad range of from about $1 \times 10^5$ Pa up to about $2 \times 10^7$ Pa, and in some cases up to about $2 \times 10^8$ Pa or higher, may be employed. Typically, the specific pressure used will be governed to some extent by the specific charge and catalyst employed. In general, pressures in the range of from about $2 \times 10^6$ Pa to about $10 \times 10^6$ Pa and particularly in the range of from about $2.7 \times 10^6$ Pa to about $9 \times 10^6$ Pa are preferred.

The ratio of catalyst to the olefinic compound to be hydroformylated is generally not critical and may vary widely. It may be varied to achieve a substantially homogeneous reaction mixture. Solvents are therefore not required. However, the use of solvents which are inert, or which do not interfere to any substantial degree with the desired hydroformylation reaction under the conditions employed, may be used. Saturated liquid hydrocarbons, for example, may be used as solvent in the process, as well as alcohols, ethers, acetonitrile, sulfolane, and the like. The molar ratio of catalyst to the olefinic compound in the reaction zone at any given instant is typically at least about 1:1000000, preferably at least about 1:10000, and more preferably at least about 1:1000, and preferably at most about 10:1. A higher or lower ratio of catalyst to olefinic compound may, however, be used, but in general it will be less than about 1:1.

The hydrogen and carbon monoxide may be introduced into the process of the present invention as two discreet feed streams, i.e. a hydrogen gas feed stream and a carbon monoxide gas feed stream, or as a combined feedstream, e.g. a syngas feedstream.

The total molar ratio of hydrogen to carbon monoxide in the feedstream may vary widely. In general, a mole ratio of at least about 1:1, hydrogen to carbon monoxide, is employed. Suitably, ratios of hydrogen to carbon monoxide comprise those within the range of from about 1:1 to about 10:1. Higher or lower ratios may, however, be employed.

The ratio of hydrogen to carbon monoxide employed will be governed to some extent by the nature of the reaction product desired. If conditions are selected that will result primarily in an aldehyde product, only about one mole of hydrogen per mole of carbon monoxide enters into reaction with the olefinic compound. When an alcohol is the preferred product of the process of the present invention, about two moles of hydrogen and about one mole of carbon monoxide react with each mole of olefinic compound. The use of ratios of hydrogen to carbon monoxide which are somewhat lower than those defined by these values is generally preferred.

The organophosphine modified cobalt hydroformylation catalyst for use in the process of the present invention comprises cobalt in complex combination with carbon monoxide and an organophosphine ligand. By the term "complex combination" as used herein, is meant a coordination compound formed by the union of one or more carbon monoxide and organophosphine molecules with one or more cobalt atoms. In its active form the suitable organophosphine modified cobalt hydroformylation catalyst contains one or more cobalt components in a reduced valence state.

Suitable organophosphine ligands include those having a trivalent phosphorus atom having one available or unshared pair of electrons. Any essentially organic derivative of trivalent phosphorus with the foregoing electronic configuration is a suitable ligand for the cobalt catalyst.

Organic radicals of any size and composition may be bonded to the phosphorus atom. For example the organophosphine ligand may comprise a trivalent phosphorus having aliphatic and/or cycloaliphatic and/or heterocyclic and/or aromatic radicals satisfying its three valencies. These radicals may contain a functional group such as carbonyl, carboxyl, nitro, amino, hydroxy, saturated and/or unsaturated carbon-to-carbon linkages, and saturated and/or unsaturated non-carbon-to-carbon linkages.

It is also suitable for an organic radical to satisfy more than one of the valencies of the phosphorus atom, thereby forming a heterocyclic compound with a trivalent phosphorus atom. For example, an alkylene radical may satisfy two phosphorus valencies with its two open valencies and thereby form a cyclic compound. Another example would be an alkylene dioxy radical that forms a cyclic compound where the two oxygen atoms link an alkylene radical to the phosphorus atom. In these two examples, the third phosphorus valency may be satisfied by any other organic radical.

Another type of structure involving trivalent phosphorus having an available pair of electrons is one containing a plurality of such phosphorus atoms linked by organic radicals. This type of a compound is typically called a bidentate ligand when two such phosphorus atoms are present, a tridentate ligand when three such phosphorus atoms are present, and so forth.

Suitable organophosphine modified cobalt hydroformylation catalysts for use in the process of the present invention and their methods of preparation are disclosed in U.S. Pat. Nos. 3,369,050, 3,501,515, 3,448,158, 3,448,157, 3,420,898 and 3,440,291, all of which are incorporated herein by reference. Preferably, the organophosphine modified cobalt hydroformylation catalyst is substantially homogeneous with the reaction mixture.

Preferred organophosphine modified cobalt hydroformylation catalysts for use in the process of the present invention are those which include an organic tertiary phosphine ligand, especially a bicyclic heterocyclic tert-phosphine ligand, preferably as disclosed in U.S. Pat. No. 3,501,515. Representative examples of such ligands include:
9-hydrocarbyl-9-phosphabicyclo[4.2.1]nonane;
9-aryl-9-phosphabicyclo[4.2.1]nonane,
such as 9-phenyl-9-phosphabicyclo[4.2.1]nonane;
(di)alkyl-9-aryl-9-phosphabicyclo[4.2.1]nonane,
such as 3,7-dimethyl-9-phenyl-9-phosphabicyclo[4.2.1]-nonane and
3,8-dimethyl-9-phenyl-9-phosphabicyclo[4.2.1]nonane;
9-alkyl-9-phosphabicyclo[4.2.1]nonane,
such as 9-octadecyl-9-phosphabicyclo[4.2.1]nonane,
9-hexyl-9-phosphabicyclo[4.2.1]nonane,
9-eicosyl-9-phosphabicyclo[4.2.1]nonane, and
9-triacontyl-9-phosphabicyclo[4.2.1]nonane;
9-cycloalkyl-9-phosphabicyclo[4.2.1]nonane,
such as 9-cyclohexyl-9-phosphabicyclo[4.2.1]nonane and
9-(1-octahydropentalyl)-9-phosphabicyclo[4.2.1]nonane;
9-cycloalkenyl-9-phosphabicyclo[4.2.1]nonane, such as 9-cyclooctenyl-9-phosphabicyclo[4.2.1]nonane;
9-hydrocarbyl-9-phosphabicyclo[3.3.1]nonane;
9-aryl-9-phosphabicyclo[3.3.1]nonane,
such as 9-phenyl-9-phosphabicyclo[3.3.1]nonane;
9-alkyl-9-phosphabicyclo[3.3.1]nonane,
such as 9-hexyl-9-phosphabicyclo[3.3.1]nonane, and
9-eicosyl-9-phosphabicyclo[3.3.1]nonane, and mixtures thereof.

A particularly preferred ligand includes a 9-eicosyl-9-phosphabicyclononane compound. A particularly preferred organophosphine modified cobalt hydroformylation catalyst includes a derivative thereof, believed to be a complex comprising cobalt.

The organophosphine modified cobalt hydroformylation catalysts can be prepared by a diversity of methods well known to those skilled in the art as disclosed in U.S. Pat. Nos. 3,369,050, 3,501,515, 3,448,157, 3,420,898 and 3,440,291. A convenient method is to combine a cobalt salt, organic or inorganic, with the desired phosphine ligand, for example, in liquid phase followed by reduction and carbonylation. Suitable cobalt salts comprise, for example, cobalt carboxylates such as acetates, octanoates, etc. as well as cobalt salts of mineral acids such as chlorides, fluoride, sulfates, sulfonates, etc. as well as mixtures of one or more of these cobalt salts. The valence state of the cobalt may be reduced and the cobalt-containing complex formed by heating the solution in an atmosphere of hydrogen and carbon monoxide. The reduction may be performed prior to the use of the organophosphine modified cobalt hydroformylation catalysts or it may be accomplished in-situ with the hydroformylation process in the hydroformylation zone. Alternatively, the organophosphine modified cobalt hydroformylation catalysts can be prepared from a carbon monoxide complex of cobalt. For example, it is possible to start with dicobalt octacarbonyl and, by mixing this substance with a suitable phosphine ligand, the ligand replaces one or more of the carbon monoxide molecules, producing an organophosphine modified cobalt hydroformylation catalyst; the active catalyst compound is typically formed under process conditions.

The feedstock composition of the process of the present invention comprises a compound having at least one olefinic carbon-to-carbon bond. Commonly, the feedstock composition of the process of the present invention comprises more than one compound having at least one olefinic carbon-to-carbon bond.

The process of the present invention is generally applicable to the hydroformylation of any optionally substituted aliphatic or cycloaliphatic compound having at least one olefinic carbon-to-carbon bond. If the aliphatic or cycloaliphatic compound having at least one olefinic carbon-to-carbon bond is substituted, the substituent will typically be inert under reaction conditions. Examples of suitable substituents include aromatic rings, alcohol groups, amine groups, silane groups and the like. Thus, the process of the present invention may be applied to the hydroformylation of olefinic compounds having, for example, from 3 to 40 carbon atoms, to produce alcohols, or under certain conditions a mixture of aldehydes and alcohols, having one more carbon atom than the starting olefinic compound. In particular, the process of the present invention may be applied to the hydroformylation of olefinic compounds having, for example, from 3 to 40 carbon atoms, to produce alcohols having one more carbon atom than the starting olefinic compound in a single step. Mono-olefinic compounds, such as propylene, butylenes, amylenes, hexylenes, heptylenes, octylenes, nonylenes, decylenes, undecylenes, dodecylenes, tridecylenes, tetradecylenes, pentadecylenes, hexadecylenes, heptadecylenes, octadecylenes, nonadecylenes, and their homologues, are examples of suitable unsaturated compounds which may be hydroformylated in the process of the present invention. Suitable unsaturated compounds include both branched and straight-chain compounds having one or more olefinic sites. When two or more double bonds are present these may be conjugated, as in 1,3-hexadiene, or non-conjugated. In the case of polyolefinic compounds, it is possible to hydroformylate only one of the olefinic sites or several or all of these sites. The unsaturated carbon-to-carbon olefinic linkages may be between terminal and their adjacent carbon atoms, as in 1-pentene, or between internal chain carbon atoms, as in 4-octene.

In one embodiment of the present invention, at least one of the compounds having at least one olefinic carbon-to-carbon bond used in the process of the present invention is a mono-olefinic compound. In another embodiment of the present invention, substantially all of the feedstock having at least one olefinic carbon-to-carbon bond are mono-olefinic compounds.

In another embodiment of the present invention, at least one of the compounds having at least one olefinic carbon-to-carbon bond used in the process of the present invention has an olefinic linkage between a terminal carbon atom and its adjacent carbon atom, these can also be referred to as terminal or alpha olefins. In another embodiment of the present invention, substantially all of the feedstock having at least one olefinic carbon-to-carbon bond have an olefinic linkage between a terminal carbon atom and its adjacent carbon atom.

In an alternative embodiment of the present invention, at least one of the compounds having at least one olefinic carbon-to-carbon bond used in the process of the present invention has an internal olefinic bond. In another alternative embodiment of the present invention, substantially all of the feedstock having at least one olefinic carbon-to-carbon bond have an internal olefinic bond.

In another embodiment of the present invention, at least one of the compounds having at least one olefinic carbon-to-carbon bond used in the process of the present invention is a linear compound having at least one olefinic carbon-to-carbon bond. In another embodiment of the present invention, substantially all of the feedstock having at least one olefinic carbon-to-carbon bond are linear compounds having at least one olefinic carbon-to-carbon bond.

In an alternative embodiment of the present invention, at least one of the compounds having at least one olefinic carbon-to-carbon bond used in the process of the present invention is a branched compound having at least one olefinic carbon-to-carbon bond. In another alternative embodiment of the present invention, substantially all of the feedstock having at least one olefinic carbon-to-carbon bond are branched compounds having at least one olefinic carbon-to-carbon bond.

By the term "substantially all" when used in relation to the feedstock composition, it is meant that at least about 70% wt., preferably at least about 75% wt., of the feedstock composition contains the specified characteristic.

Hydroformylation of macromolecular materials involving acyclic units of the above types, such as polydiolefinic compounds, for example polybutadiene, as well as copolymers of olefinic and diolefinic compounds, for example styrene-butadiene copolymer, may also be accomplished by the process of the present invention.

Cyclic compounds are equally suitable for use in the process of the present invention. Suitable cyclic compounds include unsaturated alicyclic compounds such as the cyclic olefinic compounds containing carbon-to-carbon unsaturation, such as cyclopentene, cyclohexene, and cycloheptene. Also included in this category are the terpenes and fused-ring polycyclic olefinic compounds, such as 2,5-bicyclo(2,2,1)heptadiene,1,4,4a,5,8,8a-hexahydro-1,4,5,8-dimethanonaphthalene and the like.

The process of this invention is typically used to hydroformylate olefinic carbon-to-carbon linkages of hydrocarbon feedstock compositions but may also be used for non-hydrocarbon feedstock compositions. Thus, it is possible to hydroformylate olefinically unsaturated alcohols, epoxides, aldehydes, and acids to corresponding alcohols, aldehydes, and acids containing an aldehyde or hydroxy group on one of the carbon atoms previously involved in the olefinic bond of the starting material. The following are a few specific examples of different types of olefinic compounds that may be hydroformylated by the process of the present invention and the products obtained thereby:

$$CH_3(CH_2)_3CH=CH_2+CO+H_2 \rightarrow CH_3(CH_2)_5CHO$$
and/or $CH_3(CH_2)_5CH_2OH$+isomeric products $$CH_2=CHCl+CO+H_2 \rightarrow ClCH_2CH_2CH_2OH \text{ and/or}$$
$ClCH_2CH_2CHO$ $$CH_3COOCH_2CH=CH_2+CO+$$
$H_2 \rightarrow CH_3COOCH_2CH_2CH_2CHO$ and/or
$CH_3COOCH_2CH_2CH_2CH_2OH$ cyclopentene+CO+$H_2 \rightarrow$ formylcyclopentane and/or cyclopentylcarbinol $$C_2H_5OCOCH=CHCOOC_2H_5+CO+$$
$H_2 \rightarrow C_2H_5OCOCH(CHO)CH_2COOC_2H_5$ and/or
$C_2H_5OCOC(CH_2OH)HCH_2COOC_2H_5$ allyl benzene+CO+$H_2 \rightarrow$ gammaphenylbutyraldehyde and/or delta-phenylbutanol+isomeric products Typically, the feedstock composition of the process of the present invention comprises olefinic compounds having from 3 to 40 carbon atoms per molecule. Preferably, the feedstock composition of the process of the present invention comprises olefinic compounds having from 3 to 30 carbon atoms per molecule, more preferably having from 4 to 22 carbon atoms per molecule, and most preferably having from 5 to 20 carbon atoms per molecule. In one embodiment of the present invention, the feedstock composition comprises olefinic compounds having from 6 to 18 carbon atoms per molecule.

It will be appreciated by those skilled in the art that, depending upon the specific charge and cobalt catalyst employed, the process of the present invention may effect the direct, single stage hydroformylation of an olefinic compounds to yield a reaction product wherein the alcohols predominate over the aldehydes. By selection of reaction conditions, reaction charge and the cobalt catalyst within the above defined ranges it is possible to obtain greater than or equal to 80% of straight chain alcohols, rather than various branched isomers from the hydroformylation of olefinic compounds. Typically, the alcohols are the desired end product. However, by varying the operating conditions as described hereinbefore the ratio of aldehydes to alcohols in the product may be varied.

The process of the present invention may thus be employed to effect the direct, single stage hydroformylation of olefinic compounds, preferably mono-olefinic compounds, and especially mono-olefins, having, for example, from 3 to 40 carbon atoms per molecule, preferably to produce predominantly terminal alcohols having 4 to 41 carbon atoms per molecule, respectively. Olefinic fractions, such as, for example, polymeric olefinic fractions, cracked wax fractions, and the like, containing substantial proportions of olefinic compounds, may be readily hydroformylated to fractions of hydroformylated products comprising mixtures of predominantly terminal aldehydes and alcohols having one more carbon than the olefinic compounds in the charge and wherein these alcohols are the predominant reaction product. Other suitable sources of olefinic fractions include those obtained directly or indirectly from Fischer-Tropsch reactions. Suitable feeds consisting of olefinic fractions include, for example $C_7$, $C_8$, $C_9$, $C_{10}$ and higher olefinic fractions as well as olefinic fractions of wider boiling ranges such as $C_7$-$C_9$, $C_{10}$-$C_{13}$, $C_{14}$-$C_{17}$ olefinic fractions and the like. In broad terms $C_8$-$C_{16}$ olefinic compounds, in particular $C_8$-$C_{16}$ olefinic hydrocarbons, are preferred.

It will be appreciated that under the above-defined conditions, the olefinic charge may react with carbon monoxide and hydrogen to form reaction products comprising aldehydes and/or alcohols having one more carbon atom per molecule than the olefin charged.

The proportions in which reactants are fed to the reaction zone may vary over relatively wide limits; for example, from about 1 to about 5 molar amounts of an olefinic compound as described hereinbefore may be reacted with from about 1 to about 12 moles of hydrogen and about 1 to about 7 moles of carbon monoxide. Sufficient amounts of olefinic compound are however included in the feed to the reaction zone.

Admixtures of promoters and/or stabilizers and the like may also be included in the process of the present invention. Thus, minor amounts of phenolic stabilizers such as hydroquinone and/or alkaline agents such as hydroxides of alkali metals, for example NaOH and KOH, may be added to the reaction zone.

The reaction mixtures obtained may be subjected to suitable catalyst and product separating means comprising one or more steps, for example, stratification, solvent extraction, distillation, fractionation, adsorption, filtration, etc. The specific method of product and catalyst separation employed will be governed to some extent by the specific complex and reactants charged. Catalyst or components thereof, as well as unconverted charge, and solvent, when employed, may be recycled in part or its entirety to the reaction zones.

The preformed cobalt catalyst, or separate components of the catalyst capable of producing the active complex in situ, may be added to material separated from the reactor which is being recycled to the reaction zones. A part of an alcoholic reaction product may, if desired, be recycled to the reaction zones to function as solvent and/or diluent and/or suspending medium for the catalyst, the catalyst components, and the like, passing to the reaction zones. A part of, or all of an aldehyde product, if produced, may optionally be recycled to the reaction zones or may be subjected to hydrogenation or hydroformylation conditions in a separate reaction zone in the presence of a cobalt catalyst. The cobalt catalyst used for the optional separate hydroformylation of any aldehydes produced need not be the same as that used in the first step.

The invention will be further described by way of the following non-limiting examples.

EXAMPLES

All of the examples were performed using a reactor assembly which is comprised of four individual reactors, each of 2 litre in volume, connected in series. A continuous stream of olefin feedstock (280 g/h), NEODENE-1112 or NEODENE-1314 olefins from Shell (NEODENE is a Shell trade mark), catalyst components (cobalt octoate, P-ligand (9-eicosyl-9-phosphabicyclononane), from Shell, and KOH), fresh syngas (inlet ratio $H_2/CO=1.7$) and recycle catalyst, is fed in to the first reactor. The pressure in the first reactor is maintained at $5 \times 10^6$ Pa.

After depressurization, the product alcohols, formed by hydroformylation of the olefin feed stream and the catalyst dissolved in heavy by-products are separated via a short-path distillation. The heavy-bottom stream containing the cobalt catalyst is recycled back to the first reactor. The experiment was carried out in a continuous mode.

Feed rates of catalyst components are adjusted to maintain the targeted catalyst concentration and composition: 0.3 wt % cobalt, P-ligand/Co=1.3, and KOH/Co=0.5, unless otherwise stated.

All of the examples were performed using the following solutions of catalyst components: 10% wt of $Co(octoate)_2$ dissolved in the respective product alcohol, 7.5% wt of P-ligand dissolved in the respective olefin feedstock solution and 1% wt of potassium hydroxide, dissolved in the respective product alcohol. The respective product alcohol used is the alcohol composition formed by the hydroformylation of the olefin feedstock of the example. The respective olefin feedstock composition is the olefin feedstock composition used in the example.

Example 1 (Comparative)

An olefin feedstock composition of NEODENE-1112 olefins from Shell, which comprises a mixture of linear $C_{11}$ and $C_{12}$ olefins, was hydroformylated in the reactor series described above. The concentration of cobalt in the reactor series was maintained at a target concentration of 0.28% wt based on total reactor contents. The temperature of the reactors was 192° C.

The average amount of paraffin by-product formed over the test period of 288 h was 6.9% wt on total crude alcohol product. The average amount of normal 1-alcohols produced based upon the overall amount of alcohols produced during the test period 288 h was 81.0% wt. The catalyst decomposition rate, a measure for catalyst stability, was determined to be 0.1 g Co/kg of hydroformylation products produced over the test period of 288 h.

Example 2

An olefin feedstock composition of NEODENE-1112 olefins from Shell, which comprises a mixture of linear $C_{11}$ and $C_{12}$ olefins, was hydroformylated in the reactor series described above. The concentration of cobalt in the reactor series was maintained at a target concentration of 0.30% wt based on total reactor contents.

The temperature of the reactors was 182° C. for the first reactor, and 192° C. for the second, third, and fourth reactors.

The average amount of paraffin by-product formed over the test period of 240 h was 6.4% wt on total crude alcohol product. The average amount of normal 1-alcohols produced based upon the overall amount of alcohols produced during the test period of 240 h was 83.3% wt. The catalyst decomposition rate, a measure for catalyst stability, was determined to be 0.02 g Co/kg of hydroformylation products produced over the test period of 240 h.

Example 3 (Comparative)

An olefin feedstock composition of NEODENE-1314 olefins from Shell, which comprises a mixture of linear $C_{13}$ and $C_{14}$ olefins, was hydroformylated in the reactor series described above. The concentration of cobalt in the reactor series was maintained at a target concentration of 0.30% wt based on total reactor contents.

The temperature of the reactors was 192° C.

The average amount of paraffin by-product formed over the test period of 264 h was 7.3% wt on total crude alcohol product. The average amount of normal 1-alcohols produced based upon the overall amount of alcohols produced during the test period of 264 h was 79.0% wt. The catalyst decomposition rate, a measure for catalyst stability, was determined to be 0.075 g Co/kg of hydroformylation products produced over the test period of 264 h.

Example 4

An olefin feedstock composition of NEODENE-1314 olefins from Shell, which comprises a mixture of linear $C_{13}$ and $C_{14}$ olefins, was hydroformylated in the reactor series described above. The concentration of cobalt in the reactor series was maintained at a target concentration of 0.32% wt based on total reactor contents.

The temperature of the reactors was 182° C. for the first reactor, and 192° C. for the second, third, and fourth reactors.

The average amount of paraffin by-product formed over the test period of 288 h was 6.6% wt on total crude alcohol product. The average amount of normal 1-alcohols produced based upon the overall amount of alcohols produced during the test period of 288 h was 80.4% wt. The catalyst decomposition rate, a measure for catalyst stability, was determined to be 0.02 g Co/kg of hydroformylation products produced over the test period of 288 h.

It can be clearly seen from the given data that a significant reduction in the amount of paraffins produced occurs when the first reactor is run at a lower temperature than the temperature in the second, third, and fourth reactors. In particular, in an industrial process which produces alcohols on a large scale, this reduction in the formation of paraffin by-products would relate to several tons each day.

It can also be clearly seen that the amount of normal 1-alcohols produced in relation to the overall amount of alcohols produced is increased.

The average amount of cobalt consumed in the reaction is also lower when the first reactor is run at a lower temperature than the temperature in the third, fourth and fifth reactors. This reduction in the amount of cobalt consumed in the reaction reduces the amount of cobalt and/or cobalt carbide deposits building up on the internal surfaces of the process equipment.

The invention claimed is:

1. A hydroformylation process comprising reacting a feedstock composition comprising a compound having at least one olefinic carbon-to-carbon bond with hydrogen and carbon monoxide in the presence of an organophosphine modified cobalt hydroformylation catalyst, wherein the hydroformylation process is carried out in at least two reaction zones, wherein the at least two reaction zones comprise an earlier reaction zone and a later reaction zone, wherein the temperature of the later reaction zone is at least about 2° C. greater than the temperature in the earlier reaction zone, and the temperature of the later reaction zone is in the range of from about 140° C. to about 220° C., and the temperature of the earlier reaction zone is at least about 130° C.

2. The process of claim 1 wherein the temperature of the later reaction zone is in the range of from about 145° C. to about 215° C.

3. The process of claim 2 wherein the temperature of the later reaction zone is in the range of from about 150° C. to about 210° C.

4. The process of claim 1 wherein the temperature of the earlier reaction zone is at least about 135° C.

5. The process of claim 4 wherein the temperature of the earlier reaction zone is at least about 140° C.

6. The process of claim 1 wherein the organophosphine modified cobalt hydroformylation catalyst comprises cobalt in complex combination with carbon monoxide and an organophosphine ligand, wherein the organophosphine ligand has a trivalent phosphorus atom having one available or unshared pair of electrons.

7. The process of claim 6 wherein the organophosphine ligand is a bicyclic heterocyclic tert-phosphine ligand.

8. The process of claim 6 wherein the ratio of hydrogen to carbon monoxide is in the range of from about 1:1 to about 10:1.

9. The process of claim 1 wherein the compounds having at least one olefinic carbon-to-carbon bond are linear compounds having at least one olefinic carbon-to-carbon bond.

10. The process of claim 1 wherein the feedstock composition comprises olefinic compounds having from 6 to 18 carbon atoms.

11. The process of claim 1 wherein the process is carried out in more than two reaction zones.

12. The process of claim 11 wherein the temperature is increased in a step-wise fashion from one reaction zone to the next.

13. The process of claim 11 wherein there is at least one reaction zone subsequent to the reaction zone wherein the maximum temperature has been reached and the temperature of the at least one reaction zone subsequent to the reaction zone wherein the maximum temperature has been reached is reduced relative to the maximum temperature reached.

14. The process of claim 11 wherein the earlier reaction zone is preceded by at least one reaction zone wherein the temperature in said preceding reaction zone is lower than about 130° C.

15. The process of claim 1 wherein the process is carried out in at least two reactors linked in series.

* * * * *